US00PP37095P2

(12) United States Plant Patent
Osiecki

(10) Patent No.: US PP37,095 P2
(45) Date of Patent: Nov. 11, 2025

(54) ***PHILODENDRON* PLANT NAMED 'RCM2'**

(50) Latin Name: ***Philodendron* hybrid**
Varietal Denomination: RCM2

(71) Applicant: Marian Osiecki, Marianna, FL (US)

(72) Inventor: Marian Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 19/032,639

(22) Filed: Jan. 21, 2025

(51) Int. Cl.
*A01H 5/12* (2018.01)
*A01H 6/10* (2018.01)

(52) U.S. Cl.
USPC ..... Plt./381
CPC ..... *A01H 6/10* (2018.05)

(58) Field of Classification Search
USPC ..... Plt./381
See application file for complete search history.

*Primary Examiner* — Susan McCormick Ewoldt

(57) ABSTRACT

A new and distinct *Philodendron* cultivar named 'RCM2' is disclosed, characterized by dark green mature foliage with distinct salmon pink stripes. The Immature foliage is salmon pink with dark green stripes. Young foliage has bright coral red petioles and mature foliage has olive green petioles that flushed bright coral red. Plant are self-supporting, self-heading and non-vining. Plant size is appropriate for 15 cm and larger containers. The new variety is a *Philodendron*, typically produced as an ornamental plant.

2 Drawing Sheets

Figure 1:
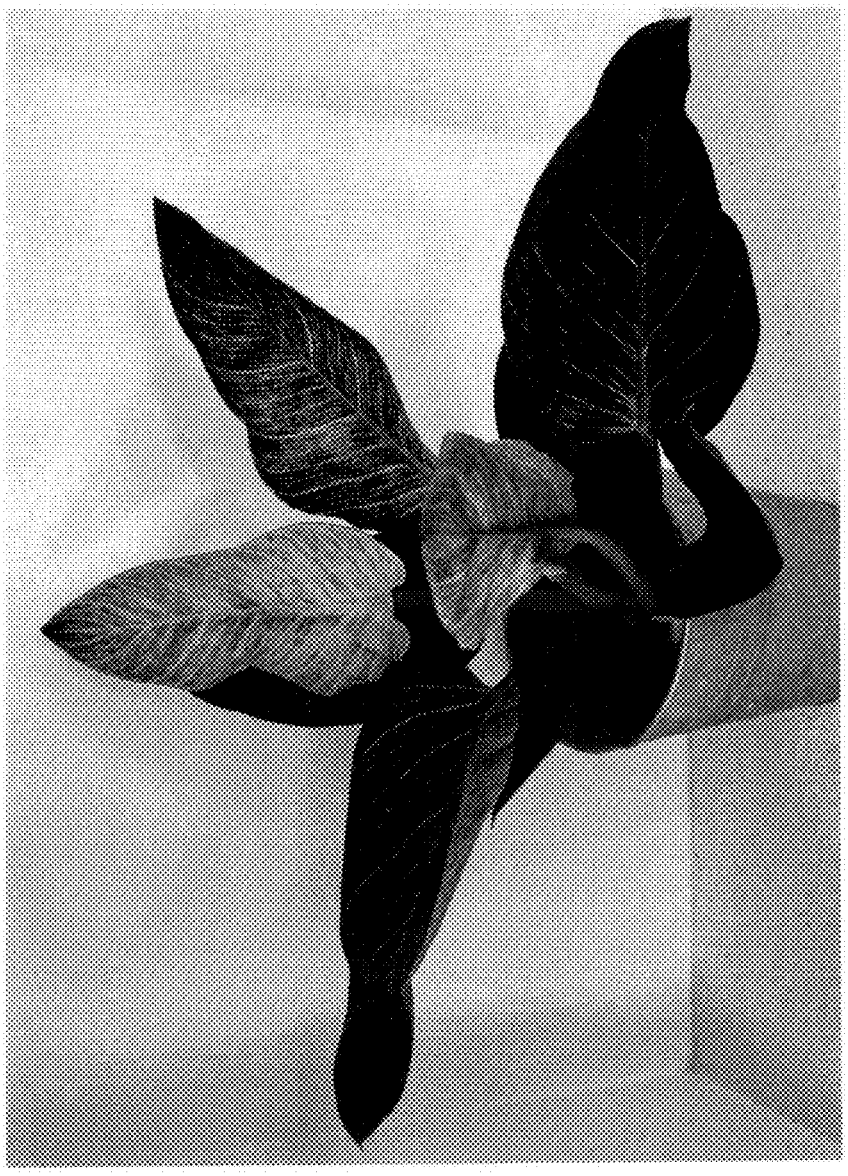

Latin name of the genus and species: *Philodendron* hybrid.

Variety denomination: 'RCM2'.

BACKGROUND OF THE INVENTION

The new cultivar is a product of a planned breeding program involving selection of naturally occurring mutations. The new variety originated as a naturally occurring whole plant selection of an undistributed, unpatented variety of *Philodendron* referred to as 'RCM1'. 'RCM1' originated as a spontaneously occurring whole plant mutation of the parent variety *Philodendron* 'Rojo Congo', U.S. Plant Pat. No. 14,116. 'RCM1' was discovered during 2020 in a greenhouse amongst other containerized plants of 'Rojo Congo' as a single plant have twisted and deformed foliage.

The inventor took vegetative cuttings of 'RCM1' to a commercial greenhouse in Altha, FL for further selection. In April of 2021 the inventor made the selection of 'RCM2' from the cuttings taken from 'RCM1'. 'RCM2' has distinct salmon pink foliar coloration without the distorted foliage of 'RCM1'.

Asexual reproduction of the new cultivar 'RCM2' was first performed at a commercial laboratory in Altha, Forida by tissue culture on Jun. 15, 2021. Subsequent propagation by tissue culture has shown that the unique features of this cultivar are stable and reproduced true to type.

SUMMARY OF THE INVENTION

The cultivar 'RCM2' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'RCM2'.

These characteristics in combination distinguish 'RCM2' as a new and distinct *Philodendron* cultivar:

1. Plant size appropriate for 15 cm and larger containers.
2. Self-heading, non-vining self-supporting mostly upright growth habit.
3. Young foliage is salmon pink with dark green stripes.
4. Mature foliage is dark green with salmon pink stripes.
5. Young foliage has bright coral red petioles.
6. Mature foliage has olive green petioles flushed bright coral red.

PARENT COMPARISON

Plants of the new cultivar 'RCM2' are similar to the unpatented seed parent 'RCM1' in most horticultural characteristics. The new variety however differs in the following characteristics:

1. Foliage of 'RCM2' is mainly flat to slightly undulating and very slightly puckered; foliage of 'RCM1' is highly twisted and deformed.

COMMERCIAL COMPARISON

'RCM2' can be compared to the commercial variety *Philodendron* 'Rojo Congo' U.S. Plant Pat. No. 14,116. Plants of *Philodendron* 'Rojo Congo' are similar to plants of 'RCM2' in most horticultural characteristics. However 'RCM2' differs from *Philodendron* 'Rojo Congo' in the following characteristics:

1. Leaf petioles of 'RCM2' are olive green with a coral red flush; mature leaf petioles of 'Rojo Congo' are purple-brown.
2. Leaves of 'RCM2' are salmon pink with dark green stripes when immature and dark green with salmon pink stripes when mature; foliage of 'Rojo Congo' is dark green.

BRIEF DESCRIPTION OF THE PHOTOGRAPHS

The accompanying photograph in FIG. 1 illustrates in full color a typical plant of 'RCM2' grown in a greenhouse in Altha, Florida. This plant is approximately 6 months old, shown in a 6 inch pot.

Figure 2:
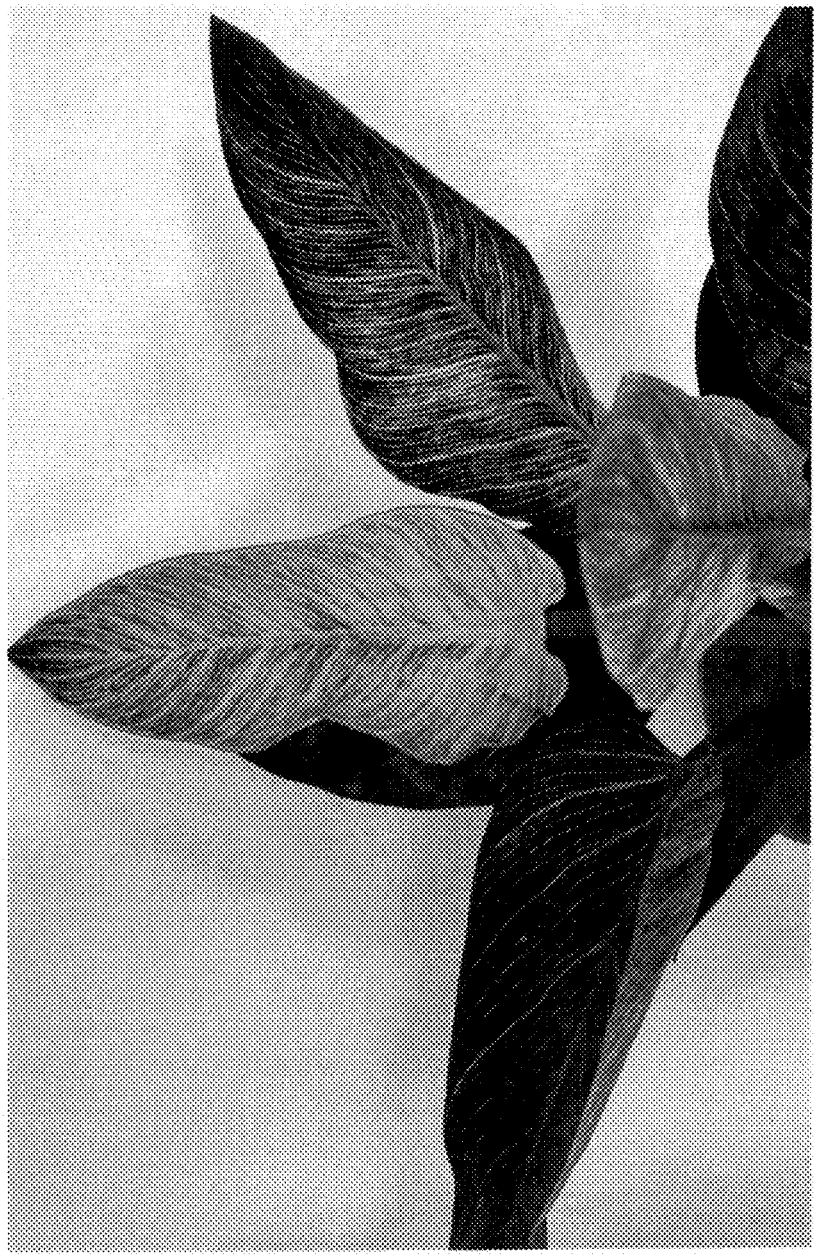

FIG. 2 is a close-up view of the foliage, at different stages of maturity.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'RCM2' plants grown in a climate controlled greenhouse in Altha, Florida, USA. Temperatures ranged from 20° C. to 25° C. at night to 25° C. to 32° C. during the day. No artificial light, photoperiodic treatments were given to the plants. Plants were grown in 80% shade, resulting in approximately 800 to 1200 foot candles of light. Measurements and numerical values represent averages of typical plant types.

Botanical classification: *Philodendron* hybrid 'RCM2'.

PROPAGATION

Root description: Thick, fleshy roots. Roots approximately 5 cm thick, colored near RHS Yellow-White 158B.

PLANT

Growth habit: Upright tender perennial. Basal leaves emerge in a slightly irregular rosette.

Plant shape: Upright, petioles and leaves slightly arching out. No stems.

Height: Approximately 40 cm to top of foliar plane.

Plant spread: Approximately 55 cm in a 6 inch pot.

Pot size of plant described: 6 inch

Growth rate: Rapid. 6 inch finished pot is ready after about 6 months.

Branching characteristics: No true branching. Leaves emerge direct from base of plant.

Age of plant described: Approximately 6 months.

FOLIAGE

Leaf:

*Arrangement*.—Single leaves emerging basally in an irregular rosette.

Largest, mature, fully expanded leaf:

*Length* (*excluding petiole*).—25 cm.

*Width*.—15 cm.

*Shape of blade*.—Elongated cordate.

*Aspect*.—Slightly undulating, mainly flat. Very slightly puckered.

*Apex*.—Apiculate.

*Base*.—Cordate, shallow lobes.

*Margin*.—Entire.

*Appearance*.—Upper surface glossy. Lower surface glossy.

*Texture of top surface*.—Glabrous.

*Texture of bottom surface*.—Glabrous.

*Color*.—Immature foliage upper side: Near RHS Red 51A striped Green NN137A. Immature foliage under side: Near RHS Red 51C faintly striped Green 137B. Mature foliage upper side: Near RHS Green NN137A heavily striped Red 54D. Mature foliage under side: Near RHS Yellow-Green 147B heavily striped Red 54D. Faint overall hue Red 51D.

Venation:

*Type*.—Pinnate.

*Venation coloration upper side immature foliage*.—Lateral veins Red 54B. Center vein, Red 54A.

*Venation coloration under side immature foliage*.—Lateral veins Red 54B. Center vein, Red 51A.

*Venation coloration upper side mature foliage*.—Lateral veins near RHS Red 54C. Center vein, Red 54D striped Green NN137A.

*Venation coloration under side mature foliage*.—Lateral veins near RHS Red 54C. Center vein, Red 51C.

Petiole:

*Length*.—Average range between 14 and 18 cm.

*Width*.—At base: Approximately 1.8 cm. At leaf attachment: Approximately 1 cm. Color: Immature: Near Red 53C. Mature: Near Yellow-Green 147C flushed Red 53A.

*Strength*.—Very strong

*Texture*.—Glabrous

INFLORESCENCE

Not observed to date.

OTHER CHARACTERISTICS

Disease resistance: Neither resistance nor susceptibility to the normal diseases and pests of *Philodendron* has been observed.

Drought tolerance and cold tolerance: The new cultivar is a typical *Philodendron*, cold tolerant to approximately 2° to 5° C. and does not tolerate drought.

Fruit/seed production: Not observed.

What is claimed is:

1. A new and distinct cultivar of *Philodendron* plant named 'RCM2' as herein illustrated and described.

* * * * *